United States Patent [19]

Aufderhaar

[11] Patent Number: 4,579,683
[45] Date of Patent: Apr. 1, 1986

[54] 5-CYANO-10-ISONITROSO-10,11-DIHYDRO-5H-DIBENZ[B,F]AZEPINE

[75] Inventor: Ernst Aufderhaar, Kaiseraugst, Switzerland

[73] Assignee: Ciba-Geigy Corporation, Ardsley, N.Y.

[21] Appl. No.: 584,057

[22] Filed: Feb. 27, 1984

Related U.S. Application Data

[62] Division of Ser. No. 498,226, May 26, 1983, Pat. No. 4,452,738, which is a division of Ser. No. 198,886, Oct. 20, 1980, abandoned.

[30] Foreign Application Priority Data

Oct. 30, 1979 [CH] Switzerland ............ 9703/79

[51] Int. Cl.$^4$ ............................ C07D 232/22
[52] U.S. Cl. ............................ 260/239 D
[58] Field of Search ............................ 260/239 D

[56] References Cited

U.S. PATENT DOCUMENTS

| | | | |
|---|---|---|---|
| 2,762,796 | 9/1956 | Morel et al. | 260/239 D |
| 3,637,661 | 1/1972 | Schindler | 260/239 D |
| 3,642,775 | 2/1972 | Schindler | 260/239 D |
| 3,716,640 | 2/1973 | Schindler | 424/244 |

FOREIGN PATENT DOCUMENTS 469340 11/1968 Japan ............................ 260/239 D Primary Examiner—Glennon H. Hollrah
Assistant Examiner—D. B. Springer
Attorney, Agent, or Firm—Michael W. Glynn; Bruce M. Collins

[57] ABSTRACT

The invention relates to a process for the manufacture of the known 5-carbamoyl-10-oxo-10,11-dihydro-5H-dibenz[b,f]azepine of the formula III which is characterized in that, for example, 5-cyano-5H-dibenz[b,f]azepine of the formula I is nitrated to form 5-cyano-10-nitro-5H-dibenz[b,f]azepine of the formula II, this is subjected to hydrolysis, then reduction, then the reduction product contained in the reaction mixture is subjected to hydrolysis and the end product of the formula III is isolated in pure form.

The process is illustrated by the following reaction scheme:

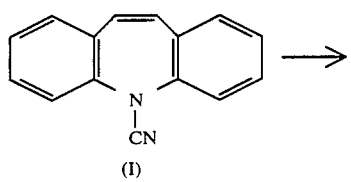

(I)

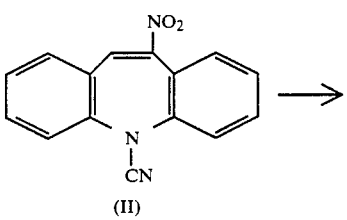

(II)

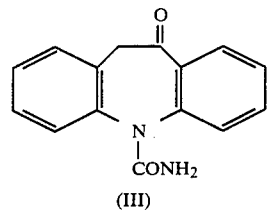

(III)

The invention relates also to new intermediates produced in these reactions.

1 Claim, No Drawings

5-CYANO-10-ISONITROSO-10,11-DIHYDRO-5H-DIBENZ[B,F]AZEPINE

This is a divisional of application Ser. No. 498,226 filed on May 26, 1983, now U.S. Pat. No. 4,452,738, issued June 5, 1984 which in turn is a divisional of application Ser. No. 198,886, filed on Oct. 20, 1980, now abandoned.

The invention relates to a new and technically advanced process for the manufacture of 5-carbamoyl-10-oxo-10,11-dihydro-5H-dibenz[b,f]azepine of the formula III which is characterized in that 5-cyano-5H-dibenz[b,f]azepine of the formula I is nitrated, the resulting 5-cyano-10-nitro-5H-dibenz[b,f]azepine of the formula II is hydrolysed to form 5-carbamoyl-10-nitro-5H-dibenz[b,f]azepine of the formula IV, the 10-nitro group in this is reduced, the reduction product is hydrolysed and the resulting end product of the formula III is isolated in pure form.

The process according to the invention is represented by the following reaction scheme:

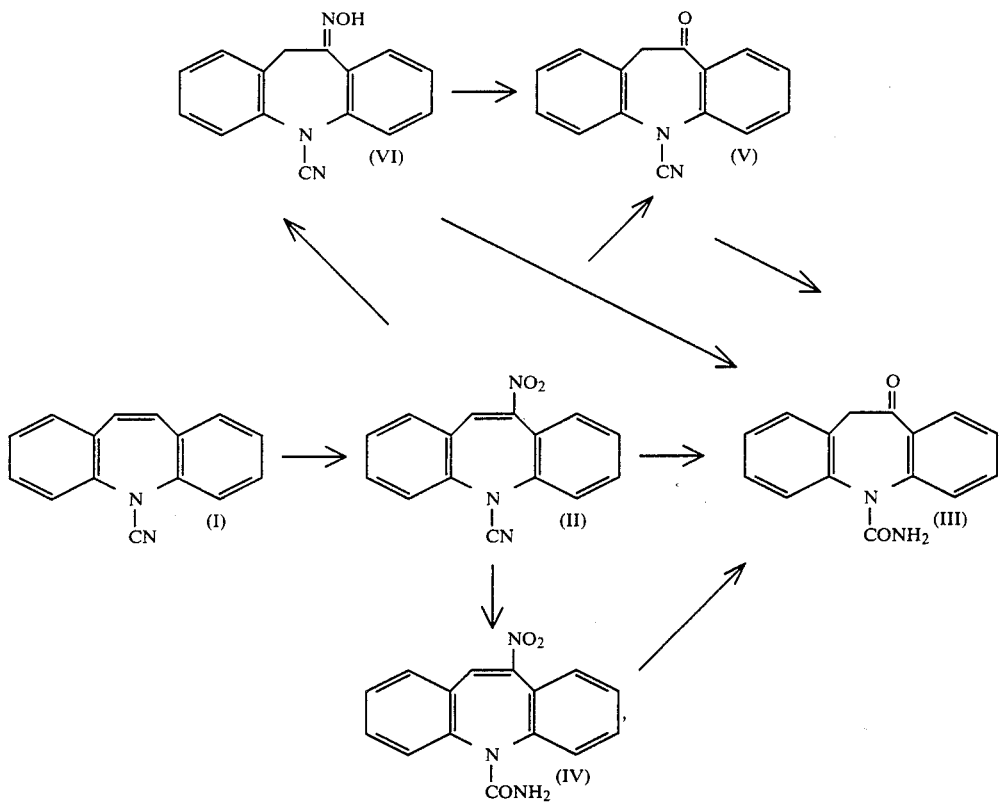

A process for the manufacture of 5-carbamoyl-10-oxo-10,11-dihydro-5H-dibenz[b,f]azepine by the hydrolysis of 10-methoxy-5H-dibenz[b,f]azepine-5-carboxamide by means of aqueous mineral acids is known from DE-OS No. 2 011 087. The manner in which this starting material can be obtained is given in Belgian Patent Specification No. 597 793, according to which, for example, 5-acetyl-5H-dibenz[b,f]azepine is brominated to form 5-acetyl-10,11-dihydro-10,11-dibromo-5H-dibenz[b,f]azepine, this is converted into 5-acetyl-10-bromo-5H-dibenz[b,f]azepine, and from this 10-methoxy-5H-dibenz[b,f]azepine is produced. This is then converted by treating with phosgene into the corresponding carbonyl chloride, from which 10-methoxy-5H-dibenz[b,f]azepine-5-carboxamide is obtained by reaction with ammonia. As compared with this manufacturing process, which is troublesome to carry out owing to its relatively large number of intermediate stages and is furthermore disadvantageous because of its high consumption of bromine, which is used only for the intermediate conversion of intermediate products, the process according to the invention comprises only few process stages, which can be carried out in a simple manner that is easy to monitor and avoids the use of costly reactants, and furthermore produces high yields of the end product of the formula III, which is obtained in a form of excellent purity.

The nitration according to the invention of the compound I to the compound of the formula II is carried out by means of customary nitrating agents, for example dinitrogen trioxide ($N_2O_3$), optionally in admixture with oxygen, for example air, or by means of dinitrogen tetroxide ($N_2O_4$), or mixtures of such compounds, or alternatively by means of nitric acid. The reaction is carried out in a suitable solvent, especially one which remains stable under the nitration conditions and does not result in undesired reactions with the nitrating agent. Especially suitable are lower alkanecarboxylic or halo-lower alkanecarboxylic acids each having up to 4 carbon atoms, for example acetic acid, propionic acid, n-butyric acid or isobutyric acid, and also, for example, trifluoroacetic or trichloroacetic acid, optionally in admixture with water, or anhydrides thereof, for example acetic acid, propionic acid, n-butyric acid, isobutyric acid or trifluoroacetic acid anhydride, or mixtures of such carboxylic acids with the corresponding anhydrides. According to a preferred embodiment of the process according to the invention, the solvents used are the anhydrides of the mentioned lower alkanecarboxylic acids, for example acetic acid anhydride, optionally in admixture with a lower alkanecarboxylic acid, for example acetic acid.

The ratio of the starting material to the amount of solvent used (weight/volume) can vary within wide limits. Advantageously the ratio of starting material to solvent is within the range of 1:3 to 1:30. The reaction temperature lies within the range of approximately 0°–120°, especially 40°–80°.

According to Chemical Reviews 36, (1945) pages 211–212, styrene reacts with nitrogen trioxide to form a mixture of nitroso and nitro compounds. Furthermore the reaction product of styrene and nitrogen trioxide is said to yield 1-nitro-2-phenylethylene if it is subjected to distillation with steam. It is also stated therein that the reaction of stilbene with nitrogen tetroxide results in 1,2-dinitro-1,2-diphenylethane. According to page 218 of the same literature source, cyclohexene reacts with dry nitrogen tetroxide in cold petroleum ether to yield the corresponding bis-nitroso-nitro derivative and oily by-products.

In J. Org. Chem. 28, (1963), pages 125–129, it is said that the reaction product of an olefin with dinitrogen tetroxide contains essentially nitro and nitroso groups of which conversion into a nitro-olefin compound requires the addition of triethylamine. So, for example, cyclooctene is reacted with dinitrogen tetroxide and the reaction product is then treated with triethylamine resulting in 1-nitrocyclooctene.

By contrast with this it has surprisingly been found that in the case of the nitration according to the invention additional operations, such as, for example, distillation with steam or treatment of the reaction mixture with triethylamine, are dispensed with and the working up, which is exceedingly simple to carry out, produces thoroughly good yields of the nitro compound of the formula II. This compound is new and is not described in the literature.

According to the invention, this is followed by the conversion of the compound of the formula II into the compound of the formula III. For this purpose, first of all the cyano group is reacted by means of hydrolysis to form the carboxamide group. Suitable methods of hydrolysis for this reaction are those which do not affect the 10-nitro group positioned at the double bond. Advantageously the hydrolysis is carried out by means of acidic agents, for example mineral acids, such as sulphuric acid, hydrochloric acid, and optionally also formic acid. Preferably boron trifluoride is used in equimolar amount or in slight excess in the form of a solution in a lower alkanecarboxylic or halo-lower alkanecarboxylic acid, for example one of the type mentioned hereinbefore, such as acetic acid or trifluoroacetic acid, and it is also possible to use discrete compounds of boron trifluoride with one of the mentioned carboxylic acids, such as acetic acid, for example one of the formula BF$_3$.2CH$_3$COOH. To carry out the hydrolysis a further inert solvent is optionally added to the reaction mixture, for example one of aromatic character, such as, for example, chlorobenzene. This is followed by treatment of the reaction mixture or of the resulting addition compound, optionally isolated in pure form, of the compound of the formula IV with BF$_3$, with hydrolysing agents, for example water, yielding 5-carbamoyl-10-nitro-5H-dibenz[b,f]azepine of the formula IV in pure form.

The hydrolysis of a nitrile group to a carboxamide group by means of boron trifluoride in the presence of acetic acid is known from J. Org. Chemistry 20, (1955), 1448. The method of operation described therein requires high temperatures, a large excess of boron trifluoride and the use of aqueous acetic acid, which together with boron trifluoride forms extremely corrosive solutions with the consequence that its industrial use, especially at high temperatures, is limited, and it can be used in industrial apparatus only under specific conditions.

By contrast, the process according to the invention permits the use of boron trifluoride in only equimolar amounts, or in slight excess, in anhydrous solvents at room temperature. A further advantage is that a discrete addition compound of boron trifluoride with the hydrolysis product of the formula IV can be isolated in good purity and in almost quantitative yield even from reaction mixtures containing a large amount of impurities, and can be converted into a pure hydrolysis product of the formula IV by treating with water.

This is followed in accordance with the invention by the conversion of the resulting intermediate of the formula IV, optionally without isolating it in pure form, into the end product of the formula III. For this purpose the compound of the formula IV is subjected to reducing conditions, for example the action of catalytically activated hydrogen, such as hydrogen in the presence of a hydrogenating catalyst, for instance a nickel or noble metal catalyst, for example Raney nickel, or in the presence of a palladium-on-carbon catalyst, in a suitable solvent, for instance a lower alkanol having up to 4 carbon atoms, such as methanol or ethanol, or the action of nascent hydrogen, for example by means of a suitable metal, such as zinc or, if desired, zinc amalgam, especially iron in an acid, for example a mineral acid, such as dilute sulphuric acid, or a carboxylic acid, such as a lower alkanecarboxylic acid, for example one of those mentioned above, such as acetic acid, or the action of a chemical reducing agent, for example tin(II) chloride.2H$_2$O, the resulting reduction product is hydrolysed in the same reaction mixture, for example by means of water, and the end product of the formula III is isolated in pure form. This is obtained in some cases in very good yield and excellent purity.

It is also possible to proceed by hydrolysing the compound of the formula II by means of acidic agents, for example such as those mentioned, such as, for example, boron trifluoride in acetic acid, optionally in the presence of a further, inert solvent, for example one of aromatic character, such as chlorobenzene, in the presence of water, and then reducing the compound of the formula IV contained in the reaction mixture, without isolating it, for example as mentioned, for example by means of catalytically activated hydrogen, such as hydrogen in the presence of a hydrogenating catalyst, such as a nickel or noble metal catalyst, for example Raney nickel, or a palladium-on-carbon catalyst, or by means of nascent hydrogen, for instance as mentioned for example iron in an acid, such as a mineral acid, for example aqueous hydrochloric acid, or a lower alkanecarboxylic or halo-lower alkanecarboxylic acid, for instance as mentioned, for example acetic acid, or the BF$_3$/acetic acid/water mixture already present in the reaction mixture. The reduction product present in the reaction mixture is then or simultaneously hydrolysed, without isolation, by means of an acidic agent, for instance as mentioned, for example by means of an aqueous acid, for instance the BF$_3$/acetic acid/water mixture present in the reaction mixture, and the resulting end product of the formula III is isolated in pure form.

The compound of the formula IV and its adduct with boron trifluoride is new and is not described in the literature.

A variant of the process according to the invention for the manufacture of the end product of the formula III is characterised in that the 10-nitro group in the compound of the formula II is reduced, the reduction product is hydrolysed, the resulting 5-cyano-10-oxo-10,11-dihydro-5H-dibenz[b,f]azepine of the formula V is hydrolysed and the resulting end product of the formula III is isolated in pure form. This variant of the process according to the invention consists in converting the compound of the formula II into that of the formula V and producing from this the end product of the formula III. Accordingly, the nitro group in the 5-cyano-10-nitro-5H-dibenz[b,f]azepine of the formula II is reduced according to one of the above-described methods and the intermediate resulting in the reaction mixture is converted by means of hydrolysis into the compound of the formula V. The reduction can, as mentioned hereinbefore, be carried out, for example, by means of catalytically activated hydrogen, such as hydrogen in the presence of a hydrogenating catalyst, for instance a nickel or noble metal catalyst, for example Raney nickel, or a palladium-on-carbon catalyst, in a suitable solvent, for example a lower alkanol having up to 4 carbon atoms, for example methanol or ethanol, or by means of nascent hydrogen, for instance by means of a suitable metal, such as zinc or, if desired, zinc amalgam or especially iron in an acid, for example a mineral acid, such as dilute sulphuric acid or concentrated hydrochloric acid, or a lower alkanecarboxylic acid, for instance one of those mentioned above, for example acetic acid, or by means of a chemical reducing agent, such as, for example, tin(II) chloride.2H$_2$O. Additional solvents, for instance a lower alkanol having 1 to 4 carbon atoms, for example ethanol, or a lower alkoxy-lower alkanol having up to 4 carbon atoms in each of the lower alkoxy and lower alkanol moieties, for example 2-methoxyethanol or 2-ethoxyethanol, and/or a solvent of aromatic character, for example an optionally lower alkylated, such as methylated, or halogenated, such as chlorinated, benzene, such as benzene, toluene or chlorobenzene, can be used in the reduction process. The reaction temperature lies in the range of from 10° to 100°, preferably 30°–70°. The reaction mixture is then, advantageously after removing insoluble components, subjected to hydrolysis, for example the action of water and, after working up, 5-cyano-10-oxo-10,11-dihydro-5H-dibenz[b,f]azepine of the formula V is isolated in pure form and is obtained in good yields and excellent purity. This compound is new and is not described in the literature. A preferred embodiment of the described conversion of the compound of the formula II into that of the formula V consists in using for the reduction by means of a metal, for example iron, as described above, a solvent that keeps resulting metal salts, for example iron salts, in solution and thus substantially prevents the production of a precipitate that is difficult to filter, such as one in the form of a sludge. Solvents of this type are, for example, strongly polar organic solvents, for instance lower alkyl ethers of ethylene glycol, in which lower alkyl has up to 4 carbon atoms and represents, for example, methyl or ethyl, and accordingly may be, for example, ethylene glycol monoethyl ester.

This is followed by the conversion of the cyano group in the compound of the formula V into the carboxamide group of the end product of the formula III by means of hydrolysis. This can be carried out by means of basic or acidic agents. Suitable basic agents are, for instance, the oxides or hydroxides of alkaline earth metals or alkali metals, for example magnesium or calcium hydroxide, and also, for example, sodium hydroxide, optionally in the presence of a peroxide, such as hydrogen peroxide, or an alkali metal bicarbonate, such as sodium bicarbonate, in admixture with hydrogen peroxide, whilst suitable acidic agents are, for example, mineral acids, such as sulphuric acid or polyphosphoric acid, and also lower alkanecarboxylic or halo-lower alkanecarboxylic acids having up to 4 carbon atoms, for example formic or acetic acid or trichloroacetic or trifluoroacetic acid in admixture with mineral acids, for example concentrated sulphuric acid. Further examples of acidic agents are Lewis acids, for example boron trifluoride, which may be present in the form of a solution in a lower alkanecarboxylic acid of the type described above, such as acetic acid, or alternatively as a discrete compound, for example of the formula BF$_3$.2CH$_3$COOH. There is optionally also added to the reaction mixture a further solvent, for example one of aromatic character, such as, for instance, chlorobenzene. The reaction temperatures lie in the range of from −5° to 150°, preferably in the range of from 0° to 40°.

A variant of this method consists in that, to produce the intermediate of the formula V, the 10-nitro group in the compound of the formula II is reduced, the resulting 5-cyano-10-isonitroso-10,11-dihydro-5H-dibenz[b,f]azepine of the formula VI is isolated in pure form, and this is hydrolysed to the 5-cyano-10-oxo-10,11-dihydro-5H-dibenz[b,f]azepine of the formula V which is isolated in pure form. This process variant is characterised in that the nitro group in the compound of the formula II is reduced to give the 10-isonitroso compound corresponding to the formula VI, for instance as mentioned, for example by means of zinc dust in an acid, for instance a lower alkanecarboxylic acid of the type mentioned, such as acetic acid, optionally in the presence of an inert solvent, such as a lower alkanol of the type mentioned, for example ethanol, or by means of hydrogen in the presence of a hydrogenating catalyst, such as a noble metal catalyst, for example a palladium-on-carbon catalyst in a suitable solvent, for instance one of aromatic character, for example pyridine, and the resulting 5-cyano-10-isonitroso-10,11-dihydro-5H-dibenz[b,f]azepine of the formula VI is isolated in pure form. This is obtained in a good yield and excellent purity. The compound is new and is not described in the literature. The compound of the formula VI is then converted by means of hydrolysis into the compound of the formula V, using especially acidic agents, such as those mentioned, such as an acid, for instance a mineral acid, for example hydrochloric acid or sulphuric acid, or a lower alkanecarboxylic or halo-lower alkanecarboxylic acid, for example acetic or trifluoroacetic acid in the presence of water. There is optionally also added to the reaction mixture an additional solvent, for example one of aromatic character, such as, for example, a benzene optionally substituted by lower alkyl having up to 4 carbon atoms, such as, for instance, methyl, or by halogen, such as chlorine, for example benzene, toluene or chlorobenzene, or a lower alkanecarboxylic acid, for instance one of the type mentioned, such as, for example, acetic acid, or a lower alkanol having up to 4 carbon atoms, for example ethanol, or mixtures of such solvents are used. The compound of the formula V is isolated in pure form from the reaction mixture and is then, as described above, converted into the end product of the formula III.

A further variant of the process according to the invention for the manufacture of the end product of the formula III is characterised in that the compound of the formula VI is hydrolysed and the resulting end product of the formula III is isolated in pure form. According to this process variant, the 5-cyano group and the 10-isonitroso group in the compound of the formula VI are hydrolysed in the same reaction mixture. For example, in the compound of the formula VI the 10-isonitroso group can be converted into the 10-oxo group by means of acidic agents, for instance as stated, for example by means of a mineral acid, such as hydrochloric acid, and then the reaction mixture can be hydrolysed, for example as described, with an acid, for example a mineral acid, such as sulphuric or polyphosphoric acid, or with a carboxylic acid, for example a lower alkanecarboxylic or halo-lower alkanecarboxylic acid, such as acetic or trifluoroacetic acid, or a Lewis acid, such as boron trifluoride in the presence of a carboxylic acid, for example acetic acid, or mixtures of such acids, optionally in the presence of a further inert solvent, such as a lower alkanol having up to 5 carbon atoms, such as methanol, or ethanol, in the presence of water, and the end product of the formula III is isolated in pure form.

The invention relates especially to the process described in the Examples.

The invention relates also to new intermediates, especially those of the formulae II, IV, V and VI. The following Examples serve to illustrate the invention; temperatures are in degrees Centigrade.

EXAMPLE 1

6.0 g (0.027 mole) of 5-cyano-5H-dibenz[b,f]azepine are dissolved in a mixture of 80 ml of acetic anhydride and 20 ml of acetic acid. The mixture is heated to 50° and a solution of 5.6 g (0.08 mole) of sodium nitrite in 10 ml of water is added dropwise in the course of 1½ hours, the temperature not being allowed to exceed 55°. The mixture is maintained at 50° for a further 2 hours and then the solvent is distilled off at reduced pressure and a bath temperature of 50°. The residue is digested twice with 100 ml of ice-water each time and taken up in 80 ml of ethanol. After standing for several hours at 0°, the precipitated yellow crystals are suction-filtered and washed with a little ethanol.

The resulting 5-cyano-10-nitro-5H-dibenz[b,f]azepine melts at 175°–176° with decomposition.

Yield: 5.2 g; 72% of the theoretical yield.

The analytical and spectroscopic data agree with the accepted structure.

EXAMPLE 2

6.5 g (0.03 mole) of 5-cyano-5H-dibenz[b,f]azepine are dissolved in a mixture of 100 ml of acetic acid and 100 ml of acetic anhydride. The mixture is heated to 40° and in the course of 45 minutes 6.2 g (0.09 mole) of sodium nitrite are added whilst air is slowly passed through the solution. The temperature increases to 55° without further heating and, at the end of the addition of the nitrite, it is maintained at 55° for a further hour. The solvent is distilled off in vacuo at a bath temperature of 50°, the residue is taken up in 300 ml of toluene and shaken repeatedly with water to remove the inorganic constituents, and the toluene is distilled off in vacuo to 40 ml. The precipitated yellow product is suction-filtered and washed with a little toluene; it is identical to the 5-cyano-10-nitro-5H-dibenz[b,f]azepine according to Example 1.

Yield: 6.1 g; 77.5% of the theoretical yield.

EXAMPLE 3

19.6 g (0.09 mole) of 5-cyano-5H-dibenz[b,f]azepine are reacted, as in Example 2, in 300 ml of acetic acid and 300 ml of acetic anhydride with 18.6 g (0.27 mole) of sodium nitrite. The red-yellow syrup remaining after evaporating off the solvent is stirred thoroughly with 300 ml of water until complete solidification has occurred. Suction-filtering is carried out, followed by washing with water until neutral reaction of the filtrate, and drying in vacuo.

An identical crude product is obtained if the above reaction is carried out at a temperature of 80°–85°.

The resulting crude product is suitable for further reactions, but can also be purified as follows:

1. 23.7 g of crude product are recrystallised from isopropanol and yield a yellow crystalline material that is identical to the 5-cyano-10-nitro-5H-dibenz[b,f]azepine according to Example 1. Yield: 18.0 g; 76.2% of the theoretical yield.

2. An end product that is identical in yield and quality is obtained by digesting the crude product with acetic acid.

EXAMPLE 4

By slow dropwise addition of sulphuric acid of 20% strength to a concentrated aqueous solution of 40.0 g (0.58 mole) of sodium nitrite in a flask, nitrous gases ($N_2O_3$) are produced which are introduced by a slow air current into a solution, heated to 55°, of 10.9 g (0.05 mole) of 5-cyano-5H-dibenz[b,f]azepine in 100 ml of toluene. The amount of atmospheric oxygen supplied is kept so low that it is not possible for any explosive mixtures of toluene vapour and oxygen to form. The introduction is continued until complete reaction of the starting material has occurred (thin layer chromatography test), the $N_2O_3$ excess is expelled by a brisk nitrogen current and the toluene is evaporated off at reduced pressure at a temperature of 40°. The remaining red syrup is taken up in 100 ml of isopropanol. After standing for several hours at 5°, the crystallisate is suction-filtered and washed with a little isopropanol. The resulting 5-cyano-10-nitro-5H-dibenz[b,f]azepine is identical to the product according to Example 1.

Yield: 9.4 g; 71.7% of the theoretical yield.

EXAMPLE 5

Analogously to the method described in Example 4, nitrous gases are produced from 55.0 g (0.8 mole) of sodium nitrite in a flask, and these are impelled by means of a slow air current into a solution, maintained at 50°, of 10.9 g (0.05 mole) of 5-cyano-5H-dibenz[b,f]azepine in 110 ml of acetic acid and 110 ml of acetic anhydride. After 3 hours the reaction is complete; the solvent is then distilled off in vacuo at a bath temperature of 50°, the residue is taken up in 50 ml of isopropanol and the material that crystallises out is suction-filtered after standing at 20° for several hours. 5-Cyano-10-nitro-5H-dibenz[b,f]azepine is obtained which is identical to the product obtained according to Example 1.

Yield: 9.5 g; 72.5% of the theoretical yield.

EXAMPLE 6

Analogously to the method described in Example 4, nitrous gases are produced from 30.0 g (0.43 mole) of sodium nitrite in a flask, and these are impelled by means of a slow air current into a solution, maintained at 55°, of 10.9 g (0.05 mole) of 5-cyano-5H-dibenz[b,f]azepine in 110 ml of acetic anhydride. When the reaction is complete (thin layer chromatography test) the reaction mixture is concentrated by evaporation in vacuo at a bath temperature of 50° and the residue is taken up in 20 ml of acetic acid. The mixture is allowed to stand for 2 hours at 20°, and the crystallisate is suction-filtered and washed with a little acetic acid. 5-Cyano-10-nitro-5H-dibenz[b,f]azepine, which is identical to the product obtained according to Example 1, is obtained.

Yield: 9.1 g; 69.4% of the theoretical yield.

EXAMPLE 7

10.0 g (0.046 mole) of 5-cyano-5H-dibenz[b,f]azepine are dissolved in 100 ml of toluene at 55°. 5.0 g (0.054 mole) of $N_2O_4$ are introduced slowly into the solution from a pressure vessel while stirring, the temperature rising to 60°, then the reaction mixture is maintained at this temperature until all of the starting material has reacted (thin layer chromatography test), is then cooled to 20° and the toluene phase is dried over sodium sulphate. After concentration by evaporation in vacuo, a red oil is obtained and this is taken up in 50 ml of isopropanol. After standing for several hours at 20°, the crystals are suction-filtered and washed with a little isopropanol. The resulting 5-cyano-10-nitro-5H-dibenz[b,f]azepine is identical to the product obtained according to Example 1.

Yield: 6.7 g; 56% of the theoretical yield.

EXAMPLE 8

43.6 g (0.2 mole) of 5-cyano-5H-dibenz[b,f]azepine are dissolved in 250 ml of acetic acid at 55° and $N_2O_4$ is introduced into the solution from a pressure vessel while stirring for 2½ hours, the temperature being maintained at 55° by occasional cooling. The end of the reaction is recognised by a green colouration of the solution ($N_2O_4$ excess) and by a thin layer chromatography test. The mixture is allowed to cool, stirred for several hours at room temperature, and the resulting precipitate is then filtered off and washed with a little acetic acid. By concentrating the filtrate and taking it up in acetonitrile, a second crystallisate of 5-cyano-10-nitro-5H-dibenz[b,f]azepine is obtained, which is identical to the product obtained according to Example 1.

Total yield: 19.5 g; 37% of the theoretical yield.

EXAMPLE 9

43.6 g (0.2 mole) of 5-cyano-5H-dibenz[b,f]azepine are dissolved in 250 ml of acetic acid at 55°. 60 ml of water are added dropwise to this solution until it begins to turn turbid and then $N_2O_4$ is slowly introduced from a pressure vessel until no more starting material can be detected by thin layer chromatography. The mixture is cooled to 5° and stirred for 2 hours at this temperature and the crystallisate is then filtered off and washed with 80% acetic acid. 5-Cyano-10-nitro-5H-dibenz[b,f]azepine, which is identical to the product obtained according to Example 1, is obtained.

Yield: 42.1 g; 80% of the theoretical yield.

EXAMPLE 10

43.6 g (0.2 mole) of 5-cyano-5H-dibenz[b,f]azepine are dissolved in 175 ml of acetic acid at 55°. At this temperature $N_2O_4$ is introduced from a pressure vessel into the solution until all the starting material has reacted (thin layer chromatography test) and the product precipitates. 16.4 g (0.2 mole) of sodium acetate are then added in portions, with occasional cooling, and the temperature is maintained at 50°–55°. The mixture is then stirred at room temperature for 3 hours, filtered and the crystallisate is washed with acetic acid and water. 5-Cyano-10-nitro-5H-dibenz[b,f]azepine, which is identical to the product obtained according to Example 1, is obtained.

Yield: 36.1 g; 68.6% of the theoretical yield.

EXAMPLE 11

21.8 g (0.1 mole) of 5-cyano-5H-dibenz[b,f]azepine are dissolved in 110 ml of acetic anhydride at 55°. 10.0 g (0.1 mole) of $N_2O_4$ are introduced into this solution from a pressure vessel so slowly that no dark brown gases escape, and the temperature is maintained at 55° by occasional cooling. When the reaction is complete, a strong current of nitrogen is passes through for one hour, the mixture is then cooled to $-20°$ and this temperature is maintained for 2 hours. The yellow crystallisate is then suction-filtered and washed with a little acetonitrile to yield 5-cyano-10-nitro-5H-dibenz[b,f]azepine, which is identical to the product obtained in accordance with Example 1. The filtrate is concentrated by evaporation in vacuo to a red oil at a bath temperature of 50°. This is taken up in 10 ml of acetonitrile, left to stand for 2 hours at 5° and the second crystallisate is suction-filtered.

Total yield: 19.5 g; 74.1% of the theoretical yield.

EXAMPLE 12

21.8 g (0.1 mole) of 5-cyano-5H-dibenz[b,f]azepine are dissolved in 140 ml of acetic anhydride at 50°. 12.0 g (0.13 mole) of $N_2O_4$ are introduced slowly into this solution from a pressure vessel, while stirring, the temperature being maintained between 50° and 55° by cooling. The mixture is left to react for one hour, then a strong nitrogen current is conveyed through and 60 ml of water are slowly added, the temperature being maintained at 50° to 55° by cooling. The mixture is then cooled to 5°, left to crystallise for one hour and filtered. 5-Cyano-10-nitro-5H-dibenz[b,f]azepine, which is identical to the product obtained according to Example 1, is obtained. The filtrate is concentrated by evaporation in vacuo and, after taking up the residue in 40 ml of 80% acetic acid, yields a second crystallisate.

Total yield: 21.5 g; 81.7% of the theoretical yield.

EXAMPLE 13

43.6 g (0.2 mole) of 5-cyano-5H-dibenz[b,f]azepine are dissolved in 430 ml of acetic anhydride. 19.0 g (0.206 mole) of $N_2O_4$ are introduced into this solution from a pressure vessel, while stirring and with occasional cooling, at such a rate that the temperature does not exceed 25°. When the reaction is complete, the solution turns green and the product precipitates in the form of crystals. The product is stirred for one hour while cooling with ice and passing through a strong nitrogen current, then is filtered off and washed with a little ethyl acetate. 5-Cyano-10-nitro-5H-dibenz[b,f]azepine, which is identical to the product obtained according to Example 1, is obtained. The filtrate is concentrated by evaporation in vacuo and taken up in ethyl acetate to yield a second crystallisate.

Total yield: 42.3 g; 80.4% of the theoretical yield.

EXAMPLE 14

35.0 g (0.16 moles) of 5-cyano-5H-dibenz[b,f]azepine are suspended in 160 ml of acetic anhydride at 20°. While stirring, a solution of 14.7 g (0.16 mole) of $N_2O_4$ in 160 ml of acetic anhydride is slowly added dropwise in the course of 5 hours, the temperature being maintained between 20° and 25°. After all of the starting material has reacted (thin layer chromatograph test) the mixture is cooled for one hour to 0°–5° while passing through a strong current of nitrogen and the crystalline product is suction-filtered. 5-Cyano-10-nitro-5H-dibenz[b,f]azepine, which is identical to the product obtained according to Example 1, is obtained.

By concentrating the filtrate to 50 ml by evaporation in vacuo a second crystallisate is obtained.

Total yield: 34.6 g; 80% of the theoretical yield.

EXAMPLE 15

43.6 g (0.2 mole) of 5-cyano-5H-dibenz[b,f]azepine are dissolved in 175 ml of acetic anhydride at 50°. $N_2O_4$ is introduced into this solution from a pressure vessel in the course of two hours in such an amount that all of the starting material reacts and a slight excess of $N_2O_4$ can be detected in the waste gas. The product is left to crystallise out at 50° and then 16.5 g (0.2 mole) of sodium acetate are added in portions. After the heat evolution has subsided the mixture is stirred for a further 30 minutes at 50° and then for several hours at room temperature. After filtration and after washing the crystallisate with acetic acid and water, 5-cyano-10-nitro-5H-dibenz[b,f]azepine, which is identical to the product obtained according to Example 1, is obtained. A further 3 g of the compound can be obtained by working up the mother liquor.

Total yield: 44.1 g; 83.8% of the theoretical yield.

EXAMPLE 16

5 ml of concentrated nitric acid (approximately 64% strength) are added dropwise at 20°, while stirring, to a solution of 2.0 g of 5-cyano-5H-dibenz[b,f]azepine in 20 ml of acetic anhydride, resulting in an exothermic reaction and a change in colour to deep yellow. The mixture is allowed to react further for one hour at 20°, 40 ml of water are then added dropwise at 50° and the precipitated oils are taken up in ethyl acetate. The residue remaining after washing and evaporating the organic phase yields with acetonitrile, after standing for a relatively long time, 0.6 g of yellow crystals, which according to a liquid chromatography test contain 78% of 5-cyano-10-nitro-5H-dibenz[b,f]azepine.

EXAMPLE 17

50 ml of a solution of 15% by weight of $BF_3$ in acetic acid (=0.11 mole) are added to a suspension of 26.3 g (0.1 mole) of 5-cyano-10-nitro-5H-dibenz[b,f]azepine in 100 ml of acetic acid at room temperature. In the course of this the temperature rises slowly to 34° with complete dissolution of the starting material. 30 ml of water are added at 30° in the course of 5 minutes, resulting in a further increase in temperature to 37°. At this temperature 40 g of iron powder are added in portions over a period of 20 minutes, the temperature being maintained at 65°–70° by occasional cooling. After the exothermic reaction has subsided, stirring is continued for a further 15 minutes and then inorganic material is filtered off and washed three times with a little acetic acid. The total filtrate is added dropwise, while stirring well, to 1½ l of water and, after stirring for 2 hours, the resulting precipitate is filtered off and washed neutral with water. After drying in vacuo at 60°, 5-carbamoyl-10-oxo-10,11-dihydro-5H-dibenz[b,f]azepine is obtained, which according to the IR spectrum is identical to authentic material.

Yield: 23.0 g; 91.2% of the theoretical yield.

EXAMPLE 18

50 ml of a solution of 15% by weight of $BF_3$ in acetic acid are added rapidly to a suspension of 26.3 g (0.1 mole) of 5-cyano-10-nitro-5H-dibenz[b,f]azepine in a mixture of 260 ml of chlorobenzene and 130 ml of acetic acid and, while heating gently, a clear yellow solution is obtained. The reaction mixture is stirred for 10 minutes and then 40 g of iron powder are added in one portion. While stirring well, 100 ml of water are added dropwise in the course of 30 minutes, the temperature increasing to 65°. By external heating the temperature is maintained at 60°–65° for two hours, and the inorganic material is filtered off and washed with chlorobenzene and acetic acid. After separating the chlorobenzene phase, this is washed with water until crystallisation of the product begins. The product is concentrated in vacuo and the residue is taken up in 100 ml of methanol. After suction-filtering and washing with a little methanol, 5-carbamoyl-10-oxo-10,11-dihydro-5H-dibenz[b,f]azepine is obtained, which according to the IR spectrum is identical to authentic material.

Yield: 21.4 g; 85% of the theoretical yield.

EXAMPLE 19

50 ml of a solution of 15% by weight of $BF_3$ in acetic acid are allowed to flow rapidly into a suspension of 26.3 g (0.1 mole) of 5-cyano-10-nitro-5H-dibenz[b,f]azepine in 200 ml of acetic acid. The mixture is stirred for 45 minutes until complete dissolution occurs and the moderately exothermic reaction has subsided. At 30° 40 g of iron powder are then added and 100 ml of water are slowly added dropwise in the course of 30 minutes, the temperature rising to 65°. The reaction mixture is stirred for 15 hours at room temperature, is heated again to 60°, and the undissolved parts are filtered off and washed three times with acetic acid. The filtrate is concentrated by evaporation in vacuo to a volume of approximately 100 ml and 400 ml of water are added dropwise. The mixture is stirred for a further 2 hours, filtered and the filter cake is washed neutral with water. After drying at 50° in vacuo, 23.8 g (94.4% of the theoretical yield) of crude product are obtained and this is recrystallised from 200 ml of acetic acid/water (8:2). Pure 5-carbamoyl-10-oxo-10,11-dihydro-5H-dibenz[b,f]azepine is obtained, which according to the IR spectrum is identical to authentic material.

Yield: 19.7 g; 78% of the theoretical yield.

EXAMPLE 20

31.5 g (0.12 mole) of 5-cyano-10-nitro-5H-dibenz[b,f]azepine are suspended in 340 ml of chlorobenzene and 98 ml of a solution of 10% by weight of $BF_3$ in acetic acid are quickly added. By heating to 30° dissolution occurs and shortly after that the $BF_3$ adduct of 5-carbamoyl-10-nitro-5H-dibenz[b,f]azepine begins to precipitate. The mixture is left to crystallise for 2 hours in an ice-bath, suction-filtered and washed with benzine. The dry intermediate is dissolved in a mixture of 200 ml of acetic acid and 35 ml of water. 50 g of iron powder are added in portions over a period of 30 minutes and the temperature is maintained at approximately 60° by cooling. The mixture is stirred for a further hour at 50°, filtered and then washed with acetic acid. The filtrate is concentrated by evaporation in vacuo and the residue is taken up in 500 ml of water. The precipitated product is suction-filtered, washed neutral with water and dried in vacuo at 50°. 5-Carbamoyl-10-oxo-10,11-dihydro-5H-dibenz[b,f]azepine is obtained, which according to the IR spectrum is identical to authentic material.

Yield: 26.0 g; 86% of the theoretical yield.

EXAMPLE 21

2 ml of concentrated sulphuric acid are added dropwise to a suspension of 4.0 g (0.015 mole) of 5-cyano-10-nitro-5H-dibenz[b,f]azepine in 40 ml of acetic acid and the mixture is stirred for a further 15 hours at room temperature. 100 ml of water are gradually added to the clear solution, the precipitated material is taken up in chloroform, and the chloroform layer is washed with water and evaporated to dryness. After recrystallisation of the residue from isopropanol, pure 5-carbamoyl-10-nitro-5H-dibenz[b,f]azepine is obtained; melting point 208°–212°, yield 2.2 g, 52.4% of the theoretical yield. The analytical and spectroscopic data agree with the given structure.

EXAMPLE 22

10 g (0.038 mole) of 5-cyano-10-nitro-5H-dibenz[b,f]azepine are heated at 90°–100° in 100 ml of 98% strength formic acid for 5 hours. The mixture is allowed to cool to room temperature and 90 ml of water are then added until the mixture begins to turn turbid, the mixture is left to crystallise for 15 hours, is filtered and the crystals are washed with water and dried in vacuo at 40°. 5-Carbamoyl-10-nitro-5H-dibenz[b,f]azepine, which is identical to the product obtained according to Example 21, is obtained.

Yield: 9.1 g; 85% of the theoretical yield.

EXAMPLE 23

25 ml of a solution of 15% by weight of $BF_3$ in acetic acid are allowed to flow rapidly into a suspension of 13.1 g (0.05 mole) of 5-cyano-10-nitro-5H-dibenz[b,f]azepine in 130 ml of chlorobenzene, while stirring, and a clear brownish solution is obtained of which the temperature increases to 35°. The crystallisation, which begins after a few minutes, is completed by stirring for one hour in an ice-bath. Suction-filtering is carried out, followed by washing with chlorobenzene and drying in vacuo at 40°, resulting in 19.2 g of 5-carbamoyl-10-nitro-5H-dibenz[b,f]azepine in the form of a $BF_3$ adduct. To liberate the end product the $BF_3$ adduct is made into a slurry with 150 ml of water, stirred for 15 hours, suction-filtered and washed neutral with water. After drying, 5-carbamoyl-10-nitro-5H-dibenz[b,f]azepine, which is identical to the product obtained according to Example 21, is obtained.

Yield: 13.5 g 95.7% of the theoretical yield.

EXAMPLE 24

50 ml of a solution of 15% by weight of $BF_3$ in acetic acid is allowed to flow into a suspension of 26.3 g (0.1 mole) of 5-cyano-10-nitro-5H-dibenz[b,f]azepine in 40 ml of acetic acid and the mixture is stirred until, with spontaneous heating to 40°, complete dissolution has occurred. 10 ml of water are then added dropwise in the course of 10 minutes, the temperature of the solution increasing to 50°, this temperature is maintained for 10 minutes and then a further 300 ml of water are slowly added dropwise. The resulting crystal suspension is stirred for 1 hour at room temperature, suction-filtered, and washed neutral with water. After drying at 60° in vacuo, 5-carbamoyl-10-nitro-5H-dibenz[b,f]azepine, which is identical to the product obtained according to Example 21, is obtained.

Yield: 27.4 g; 97.5% of the theoretical yield.

EXAMPLE 25

10.0 g (0.035 mole) of 5-carbamoyl-10-nitro-5H-dibenz[b,f]azepine are dissolved in a mixture of 100 ml of acetic acid and 50 ml of concentrated hydrochloric acid and, after adding 1.0 g of palladium-on-carbon (5%), the mixture is hydrogenated at room temperature and normal pressure. After absorbing 1,700 ml (109% of the theoretical amount) of hydrogen, the hydrogenation is interrupted, the catalyst is filtered off and the filtrate is concentrated in vacuo to approximately ¼ of its volume. After adding 400 ml of water, the mixture is left to crystallise for a few hours at 5°, suction-filtered and washed neutral with water, resulting in 5-carbamoyl-10-oxo-10,11-dihydro-5H-dibenz[b,f]azepine, which according to the IR spectrum is identical to authentic material.

Yield: 7.0 g; 78.6% of the theoretical yield.

A similar result is obtained using platinum-on-carbon (5%) as catalyst.

EXAMPLE 26

7.0 g (0.025 mole) of 5-carbamoyl-10-nitro-5H-dibenz[b,f]azepine are dissolved in a mixture of 100 ml of acetic acid and 50 ml of concentrated hydrochloric acid. 12 g of iron powder are added in the course of 15 minutes, while stirring, at a temperature of 30°–40°, the mixture is stirred for a further hour at 40°, and undissolved material is filtered off whilst the mixture is still warm and washed three times with acetic acid. The filtrate is completely evaporated in vacuo, and the residue is taken up in 100 ml of water and stirred for several hours. Filtration is carried out, followed by washing with water until neutral and drying in vacuo at 60°. 5-carbamoyl-10-oxo-10,11-dihydro-5H-dibenz[b,f]azepine, which according to the IR spectrum is identical to authentic material, is obtained.

Yield: 5.5 g; 88.6% of the theoretical yield.

EXAMPLE 27

7.9 g (0.03 mole) of 5-cyano-10-nitro-5H-dibenz[b,f]azepine are suspended in 150 ml of ethanol and 50 ml of concentrated hydrochloric acid are added. 15 g of iron powder are added at a temperature of 40° in the course of 15 minutes while stirring vigorously, the temperature rising to 55°. The mixture is then stirred for one hour at 55°, and undissolved material is filtered off whilst the mixture is still warm and washed three times with 25 ml of ethanol each time. The filtrate is concentrated to a volume of 80 ml by evaporation and, while stirring slowly, 400 ml of ice-water are added. The grey-white precipitate is filtered off, washed neutral with water and dried in vacuo at 80°. 5-Cyano-10-oxo-10,11-dihydro-5H-dibenz[b,f]azepine, which melts at 154°–156° after recrystallisation from ethanol, is obtained.

Yield: 4.8 g; 68.4% of the theoretical yield.

The analytical and spectroscopic data agree with the accepted structure.

EXAMPLE 28

52.6 g (0.2 mole) of 5-cyano-10-nitro-5H-dibenz[b,f]azepine are suspended in a mixture of 400 ml of toluene and 200 ml of ethanol. On adding 130 ml of hydrochloric acid (concentrated), the material dissolves on gentle heating. The solution is heated to 40° and in the course of 10 minutes a solution of 113 g (0.5 mole) of $SnCl_2.2H_2O$ in 90 ml of concentrated hydrochloric acid is then added. The temperature increases to 55° and is then maintained at this temperature for a further 20 minutes. The mixture is allowed to cool, the organic phase is separated off and the aqueous phase is extracted repeatedly with toluene. The combined toluene extracts are washed neutral with water, dried over sodium sulphate and concentrated by evaporation in vacuo. The remaining crude product is made into a slurry with 100 ml of isopropanol, suction-filtered and washed cold with a little isopropanol. 5-Cyano-10-oxo-10,11-dihydro-5H-dibenz[b,f]azepine, which is identical to the product obtained according to Example 27, is obtained.

Yield: 29.0 g; 62% of the theoretical yield.

EXAMPLE 29

5.0 g (0.02 mole) of 5 cyano-10-nitro-5H-dibenz[b,f]azepine are dissolved at 60° in a mixture of 80 ml of ethanol and 80 ml of acetic acid. In the course of 10 minutes, 10 g of zinc dust are added in portions, while stirring, the temperature increasing to 80°. After the reaction has subsided, 40 ml of concentrated hydrochloric acid are added at room temperature. The reaction mixture is stirred for 5 hours, undissolved material is filtered off, the filtrate is evaporated to dryness and the residue is taken up in 50 ml of water. After repeated recrystallisation of the precipitated crude product, pure 5-cyano-10-oxo-10,11-dihydro-5H-dibenz[b,f]azepine, which is identical to the product obtained according to Example 27, is obtained.

Yield: 2.3 g; 50% of the theoretical yield.

EXAMPLE 30

26.3 g (0.1 mole) of 5-cyano-10-nitro-5H-dibenz[b,f]azepine are suspended in a mixture of 150 ml of acetic acid and 100 ml of concentrated hydrochloric acid. At 30°, 40 g of iron powder are added in portions in the course of 30 minutes while stirring and the temperature is maintained at 60° by cooling. The mixture is stirred for a further 30 minutes at 50°-60° C., and undissolved material is filtered off and washed with acetic acid. The filtrate has double its volume of water added to it and is extracted three times with 100 ml of methylene chloride each time. The combined organic phases are washed with water, dried over sodium sulphate and concentrated by evaporation. The crystalline residue is made into a slurry with 100 ml of isopropanol and suction-filtered. The resulting 5-cyano-10-oxo-10,11-dihydro-5H-dibenz[b,f]azepine is identical to the product obtained according to Example 27.

Yield: 21.8 g; 93.2% of the theoretical yield.

EXAMPLE 31

5.2 g (0.02 mole) of 5-cyano-10-nitro-5H-dibenz[b,f]azepine are suspended in a mixture of 100 ml of chlorobenzene and 50 ml of ethanol. On subsequent addition of 50 ml of concentrated hydrochloric acid the temperature of the mixture increases to 35°. At this temperature 20 g of iron powder are added in portions in the course of 5 minutes while stirring vigorously, and in a few minutes the temperature of the reaction mixture has increased to 60°. The mixture is then stirred for 3 hours and cooled in this time to 25°, and the iron slurry is filtered off and washed repeatedly with ethanol and water. The organic phase of the filtrate, when extracted by washing with water, dried and concentrated by evaporation, yields a crystalline crude product which is recrystallised from isopropanol. The resulting 5-cyano-10-oxo-10,11-dihydro-5H-dibenz[b,f]azepine is identical to the product obtained according to Example 27.

Yield: 3.8 g, 81% of the theoretical yield.

A reaction mixture analogously treated using toluene as solvent instead of chlorobenzene resulted in an 84% yield of the said end product.

EXAMPLE 32

26.3 g (0.1 mole) of 5-cyano-10-nitro-5H-dibenz[b,f]azepine are suspended together with 40 g of iron powder in a mixture of 250 ml of toluene and 125 ml of ethanol. 100 ml of concentrated hydrochloric acid are added dropwise in the course of 75 minutes while stirring intensively, the temperature increasing to 60°. After stirring for 10 hours at room temperature the reaction mixture is worked up analogously to the manner described in Example 31, resulting in 5-cyano-10-oxo-10,11-dihydro-5H-dibenz[b,f]azepine, which is identical to the product obtained according to Example 27.

Yield: 19.8 g; 84.6% of the theoretical yield.

EXAMPLE 33

2.0 g (0.0085 mole) of 5-cyano-10-oxo-10,11-dihydro-5H-dibenz[b,f]azepine are dissolved in 10 ml of concentrated sulphuric acid while cooling with ice and the solution is left to stand for 30 minutes at 0°-5° C. and then added dropwise to 200 ml of ice-water. The flaky precipitate is suction-filtered, washed neutral with water, dried and recrystallised from isopropanol. 5-Carbamoyl-10-oxo-10,11-dihydro-5H-dibenz[b,f]azepine, which according to the IR spectrum is identical to authentic material, is obtained.

Yield: 1.4 g; 65% of the theoretical yield.

EXAMPLE 34

A mixture of 1.0 g (0.0043 mole) of 5-cyano-10-oxo-10,11-dihydro-5H-dibenz[b,f]azepine, 8 ml of acetic acid and 2 ml of concentrated sulphuric acid is stirred for 48 hours until complete dissolution occurs. The resulting solution is added dropwise, while stirring, to 100 ml of ice-water, and the flaky precipitate is filtered off, washed neutral with water and dried at 50° in vacuo, resulting in 5-carbamoyl-10-oxo-10,11-dihydro-5H-dibenz[b,f]azepine, which according to the IR spectrum is identical to authentic material.

Yield: 0.9 g; 84% of the theoretical yield.

EXAMPLE 35

A solution of 2.0 g (0.0085 mole) of 5-cyano-10-oxo-10,11-dihydro-5H-dibenz[b,f]azepine in 20 ml of 98% strength formic acid is heated for 8 hours in a bath of 110°-120°. The solution is then introduced into 100 ml of ice-water, filtered, washed neutral with water and dried at 50° in vacuo. The resulting 5-carbamoyl-10-oxo-10,11-dihydro-5H-dibenz[b,f]azepine is, according to the IR spectrum, identical to authentic material.

Yield: 1.8 g; 84% of the theoretical yield.

EXAMPLE 36

1.0 g (0.0043 mole) of 5-cyano-10(11)-oxo-10,11-dihydro-5H-dibenz[b,f]azepine is triturated with 20 g of polyphosphoric acid and left to stand at room temperature for several days until complete dissolution occurs. Excess water is then added in small portions, and the yellowish-white precipitate is suction-filtered and washed neutral with water. After recrystallisation from chlorobenzene, 5-carbamoyl-10-oxo-10,11-dihydro-5H-dibenz[b,f]azepine, which according to the IR spectrum is identical to authentic material, is obtained.

Yield: 0.75 g; 70% of the theoretical yield.

EXAMPLE 37

5.0 ml of $H_2O_2$ (30%) is allowed to flow, at room temperature while stirring, into a suspension of 1.0 g (0.0043 mole) of 5-cyano-10-oxo-10,11-dihydro-5H-dibenz[b,f]azepine in 20 ml of methanol, and after 30 minutes 5.0 g of sodium hydrogen carbonate are added. After stirring for three hours the undissolved material is filtered off and washed once with methanol and repeatedly with water, resulting in 5-carbamoyl-10-oxo-10,11-dihydro-5H-dibenz[b,f]azepine, which according to the IR spectrum is identical to authentic material.

Yield: 0.6 g; 55% of the theoretical yield.

EXAMPLE 38

$BF_3$ gas is introduced, while stirring, into a suspension of 3.0 g (0.013 mole) of 5-cyano-10-oxo-10,11-dihydro-5H-dibenz[b,f]azepine in a mixture of 30 ml of acetic acid and 3 ml of water until the initially strongly exothermic reaction subsides, and the temperature is maintained at 50° by external cooling. The reaction solution is allowed to cool and 100 ml of water are added dropwise to the clear solution while cooling with ice, the colourless precipitate is filtered off, and the filter residue is washed neutral with water and recrystallised from acetonitrile. The resulting 5-carbamoyl-10-oxo-10,11-dihydro-5H-dibenz[b,f]azepine is, according to the IR spectrum, identical to authentic material.

Yield: 2.3 g; 71% of the theoretical yield.

EXAMPLE 39

2.0 g (0.0085 mole) of 5-cyano-10-oxo-10,11-dihydro-5H-dibenz[b,f]azepine are introduced in portions, while stirring, into 40 ml of a solution of 10% by weight of $BF_3$ in acetic acid, after which a clear solution is obtained in the course of 15 minutes at 20°. After standing for three hours, 100 ml of water are added while cooling with ice and the pH value of the solution is adjusted to 6 by adding sodium hydroxide solution. The precipitated crude 5-carbamoyl-10-oxo-10,11-dihydro-5H-dibenz[b,f]azepine is suction-filtered, washed with water and dried. According to the IR spectrum it is identical to authentic material.

Yield: 1.6 g; 74.8% of the theoretical yield.

EXAMPLE 40

10.3 g (0.055 mole) of the complex $BF_3.2CH_3COOH$ are added to a suspension of 11.7 g (0.05 mole) of 5-cyano-10-oxo-10,11-dihydro-5H-dibenz[b,f]azepine in 60 ml of acetic acid and the temperature is allowed to increase, without external cooling, to 35°, the starting material slowly dissolving. After approximately 1 hour a $BF_3$ adduct begins to crystallise out. The mixture is stirred for 4 hours at room temperature, filtered and washed with acetic acid. The intermediate is made into a slurry with 100 ml of water and, after neutralisation with sodium acetate to a pH of 6, stirring is carried out for one hour. After suction-filtering and washing with water, 9.0 g of 5-carbamoyl-10-oxo-10,11-dihydro-5H-dibenz[b,f]azepine are obtained which, according to the IR spectrum, is identical to authentic material. A further 1.2 g of the product may be obtained from the filtrate of the intermediate, after concentration by evaporation, by fractional crystallisation from methanol/water.

Total yield: 10.2 g; 81% of the theoretical yield.

EXAMPLE 41

50 ml of a solution of 15% by weight of $BF_3$ in acetic acid are added to a suspension of 23.4 g (0.1 mole) of 5-cyano-10-oxo-10,11-dihydro-5H-dibenz[b,f]azepine in 40 ml of acetic acid and the mixture is stirred until the slight heat evolution subsides. The dropwise addition of 15 ml of water results, with a temperature increase to 40°–45°, a clear, deep blue solution. The solution is maintained at 40° for 15 minutes and then a further 135 ml of water are slowly added. The resulting crystalline precipitate is stirred for several hours at room temperature, then suction-filtered and washed neutral with water. After drying at 50° in vacuo 5-carbamoyl-10-oxo-10,11-dihydro-5H-dibenz[b,f]azepine, which according to the IR spectrum is identical to authentic material, is obtained.

Yield: 24.2 g; 96.0% of the theoretical yield.

EXAMPLE 42

A mixture of 15.4 ml (0.11 mole) of the complex $BF_3.2CH_3COOH$ with 38 ml of acetic acid is allowed to flow rapidly into a suspension of 23.4 g (0.1 mole) of 5-cyano-10-oxo-10,11-dihydro-5H-dibenz[b,f]azepine in 230 ml of chlorobenzene at room temperature, while stirring. With gentle heating a clear brownish solution results, from which a crystalline $BF_3$ adduct precipitates after approximately 10 minutes. The temperature is maintained at 5° for 30 minutes, then filtration is carried out followed by washing with chlorobenzene. The dry intermediate is made into a slurry with 200 ml of water, stirred for 30 minutes, suction-filtered and washed neutral with water. After drying in vacuo at 60°, 5-carbamoyl-10-oxo-10,11-dihydro-5H-dibenz[b,f]azepine, which according to the IR spectrum is identical to authentic material, is obtained.

Yield: 24.1 g; 95.6% of the theoretical yield.

EXAMPLE 43

1.0 g (0.004 mole) of 5-cyano-10-nitro-5H-dibenz[b,f]azepine is dissolved at 60° in a mixture of 40 ml of ethanol and 20 ml of acetic acid and 2.0 g of zinc dust are added in the course of 10 minutes while stirring vigorously. Stirring is continued for a further 15 minutes, and undissolved material is filtered off warm and washed with ethanol and water. The filtrate is evaporated to dryness and taken up with 50 ml of water. After suction-filtering, washing with water and drying, crude 5-cyano-10-isonitroso-10,11-dihydro-5H-dibenz[b,f]azepine is obtained, which after recrystallisation from ethanol melts at 185° with decomposition. The analytical and spectroscopic data agree with the accepted structure.

Yield: 0.9 g; 95% of the theoretical yield.

EXAMPLE 44

50.0 g (0.19 mole) of 5-cyano-10-nitro-5H-dibenz[b,f]azepine are dissolved in 500 ml of pyridine and, after adding 10 g of palladium-on-carbon (5%), hydrogenation is carried out at room temperature and normal pressure. After 2 hours 7,960 ml (93% of the theoretical amount) of hydrogen have been absorbed and the hydrogenation comes to a standstill. The catalyst is filtered off, the solvent is evaporated off in vacuo and the remaining crude product is recrystallised from methanol/water, resulting in 5-cyano-10-isonitroso-10,11-dihydro-5H-dibenz[b,f]azepine, which is identical to the product obtained according to Example 43.

Yield: 35.6 g; 75.2% of the theoretical yield.

EXAMPLE 45

2.5 g (0.01 mole) of 5-cyano-10-isonitroso-10,11-dihydro-5H-dibenz[b,f]azepine are suspended in a mixture of 25 ml of toluene, 15 ml of ethanol and 10 ml of hydrochloric acid (concentrated). The suspension is stirred for 30 minutes at 50°, and the toluene phase is separated off and evaporated to dryness in vacuo. The crystalline residue is made into a slurry with 10 ml of isopropanol, suction-filtered and washed twice with isopropanol, resulting in 5-cyano-10-oxo-10,11-dihydro-5H-dibenz[b,f]azepine, which is identical to the product obtained according to Example 27.

Yield: 0.8 g; 35% of the theoretical yield.

EXAMPLE 46

26.3 g (0.1 mole) of 5-cyano-10-nitro-5H-dibenz[b,f]azepine are suspended in a mixture of 265 ml of ethylene glycol monoethyl ether and 75 ml of concentrated hydrochloric acid. 40 g of iron powder are added in small portions at 40° in the course of 40 minutes and the temperature is maintained at 40° by external cooling. The mixture is stirred for a further 2 hours at room temperature, is then heated to 80°, the precipitated product dissolving again, and is filtered through a heated suction filter, which is subsequently washed with ethylene glycol monoethyl ether. The crystallisation which commences in the filtrate is completed by adding 200 of ml of water. After cooling for one hour in an ice-bath, filtration is carried out followed by washing with a mixture of ethylene glycol monoethyl ether and water in a ratio of 1:1. 5-cyano-10-oxo-10,11-dihydro-5H-dibenz[b,f]azepine is obtained which is identified, by comparing the IR spectra, with material from Example 27.

Yield: 19.0 g; 81.2% of the theoretical yield.

I claim:
1. 5-Cyano-10-isonitroso-10,11-dihydro-5H-dibenz[b,f]azepine.

* * * * *